(12) United States Patent
Copeland

(10) Patent No.: US 10,611,996 B2
(45) Date of Patent: Apr. 7, 2020

(54) PRESERVATION AND STORAGE OF BIOLOGICAL SPECIMENS

(71) Applicant: Oxyrase, Inc., Mansfield, OH (US)

(72) Inventor: James C. Copeland, Mansfield, OH (US)

(73) Assignee: OXYRASE, INC., Mansfield, OH (US)

( * ) Notice: Subject to any disclaimer, the term of this patent is extended or adjusted under 35 U.S.C. 154(b) by 93 days.

(21) Appl. No.: 15/416,903

(22) Filed: Jan. 26, 2017

(65) Prior Publication Data

US 2017/0218325 A1 Aug. 3, 2017

Related U.S. Application Data

(60) Provisional application No. 62/288,042, filed on Jan. 28, 2016.

(51) Int. Cl.
*C12N 1/04* (2006.01)
*A01N 1/02* (2006.01)

(52) U.S. Cl.
CPC .............. *C12N 1/04* (2013.01); *A01N 1/0221* (2013.01); *A01N 1/0284* (2013.01)

(58) Field of Classification Search
None
See application file for complete search history.

(56) References Cited

U.S. PATENT DOCUMENTS

| 5,432,083 A * | 7/1995 | Copeland ................ A23D 9/06 435/271 |
| 2007/0105186 A1 | 5/2007 | Gibson |
| 2013/0137770 A1* | 5/2013 | Lewis ................ A61K 9/0019 514/560 |

FOREIGN PATENT DOCUMENTS

WO        WO-03040285 A1 *   5/2003   ............. C12Q 1/045

OTHER PUBLICATIONS

Bruinsma et al., "Supercooling preservation and transplantation of the rat liver", Nature Protocols 2015, vol. 10, pp. 484-494. (Year: 2015).*
Mazur RT AL., "The enhancement of the ability of mouse sperm to survive freezing and thawing by the use of high concentrations of glycerol and the presence of an *Escherichia coli* membrane preparation (Oxyrase) to lower the oxygen concentration", Cryobiology, May 2000, vol. 40, No. 3, pp. 187-209.
Dong et al., "Antioxidants, Oxyrase, and mitochondrial uncoupler 2,4-dinitrophenol improved postthaw survival of rhesus monkey sperm from ejaculates with low cryosurvival", Fertility and Sterility, Nov. 2010, vol. 94, No. 6, pp. 2359-2361.
International Search Report and Written Opinion from PCT/US2017/015131 dated Mar. 30, 2017.

* cited by examiner

*Primary Examiner* — Michelle F. Paguio Frising
(74) *Attorney, Agent, or Firm* — Fay Sharpe LLP

(57) ABSTRACT

Methods of preserving and storing biological specimens, particularly anaerobe microorganisms are disclosed. A composition containing oxygen scavenging membrane fragments and a cryoprotectant is administered to the specimens. The specimens are then stored at a temperature that is lower than 0° C. and greater than −70° C. Cryogenic freezing is not required.

11 Claims, 2 Drawing Sheets

PRESERVATION AND STORAGE OF BIOLOGICAL SPECIMENS

CROSS-REFERENCE TO RELATED APPLICATIONS

This application claims priority to U.S. Provisional Patent Application Ser. No. 62/288,042, filed Jan. 28, 2016. The disclosure of this application is hereby fully incorporated by reference herein.

BACKGROUND

The present disclosure relates to methods for preserving and storing biological specimens, such as anaerobe microorganisms. Compositions for use in such methods are also disclosed. This preserves the specimens for later usage, and also enables recovery of the stored specimens at numbers near those initially placed in storage.

Temperature is a key parameter for storing biological specimens such as cells, tissues, and particularly anaerobe microorganisms. Specimens are usually stored in some form of container (box, tube, etc.) that is kept at room temperature, cold temperatures (refrigerated at 5-8 degrees Celsius), or frozen temperatures (sub-zero, i.e. below 0 degrees Celsius). Frozen temperatures are ordinarily about minus twenty (−20) degrees Celsius, while frozen temperatures suitable for cryogenic storage are usually about minus seventy (−70) degrees Celsius or lower. Generally, the colder the temperature, the longer the intended storage time for the specimens. Freezing or sub-zero temperatures reduce the occurrence of chemical reactions, producing a static condition, which in turn acts to protect the specimens from damage during storage.

Freezing has evolved as a method of choice, and cryofreezing in particular has become the most used storage temperature range for biological materials. However, some problems can occur in freezing biological materials. The most cited problem is ice formation. Since biological materials are high in water content (about 80% on average), the formation of ice crystals is almost inevitable. Ice crystals are thought to produce physical damage to cells and tissues. Cell damage mostly occurs during the freezing step, although damage can occur during thawing as well. Damage, as measured by cell death of the original cell population to be frozen, may range from 20% to over 90% depending upon methods and materials used and the nature of the biological material. This damage may be significant to the point that any survivors of freezing may constitute a small part of the initial population so as to not be representative of that population.

Another way to store biological materials is to employ freeze drying, or lyophilization. This method involves bringing the material to freezing temperatures while removing moisture. The end product is a dried powder.

After restoring the lyophile, the recovered portion of viable cells can be very low compared to the initial cell population that was preserved, e.g. less than 1:100 of cells (recovered:initial) are recovered (i.e. 1%). In some cases, the recoverable portion of cells may be only one cell per million initial cells, or less. This can raise the question of whether the recovered cells are truly representative of the initially frozen population. Thus, preservation/storage methods that retain a higher percentage of the initial population are favored.

One way to prevent or limit ice crystal damage to tissue is to bring the material to a "glass" state in which ice crystals are not formed. In the glass state, ice is considered to be an amorphous solid in which the water molecules are arranged randomly compared to "regular" ice, in which the water molecules are arranged in a hexagonal lattice. The production of amorphous ice depends on a fast rate of cooling to about −137 degrees Celsius. If ice crystals are not formed, then freezing damage does not occur.

BRIEF DESCRIPTION

Disclosed in various embodiments herein are methods and compositions therein for storing biological specimens. Generally speaking, the biological specimen is suspended in a composition containing at least one cryoprotectant and oxygen reducing membrane fragments. The suspension is then subjected to sub-zero temperatures. Significantly, cryogenic temperatures do not need to be used, which can reduce costs and make working with such cells faster and easier. This combines the protective effects of Oxyrase® treatment with the static conditions of sub-zero (but not cryogenic) storage. The cryoprotectant prevents the suspended cells of the biological specimen from freezing, reducing or eliminating damage that usually accompanies freezing and thawing, while not being harmful to the suspended cells.

In one aspect, the present disclosure is directed to compositions, and methods of utilizing the same, for preserving biological materials for a prolonged period of time at temperatures that normally freeze these materials. The compositions do not freeze because they contain a cryoprotectant at a level that prevents the composition from forming ice crystals. The compositions contain a cryoprotectant and oxygen scavenging membrane fragments. A sample of the biological specimen is suspended in the composition, and then stored at sub-zero temperatures.

The oxygen scavenging membrane fragments can be derived from the cytoplasmic membranes of *Escherichia coli*, *Salmonella typhimurium*, *Gluconobacter oxydans*, *Pseudomonas aeruginosa*, or *Acetobacter*. In particular embodiments, the oxygen scavenging membrane fragments are derived from *Escherichia coli*.

The composition can further comprise a hydrogen donating substance. In particular embodiments, the hydrogen donating substance is lactic acid, succinic acid, alpha-glycerol phosphate, formic acid, malic acid, or a salt thereof. The hydrogen donating substance may be present in the amount of about 1 wt % to about 5 wt % of the composition.

The composition may be in the form of a suspension. The composition may contain the oxygen scavenging membrane fragments in an amount of about 0.01 units per milliliter to about 100 units per milliliter (u/mL), or greater than 0.01 u/mL, or greater than 0.5 u/mL, or greater than 1 u/mL, or an amount from 1 u/mL to 10 u/mL, or from 5 u/mL to 10 u/mL, or from 10 u/mL to 50 u/m L.

The sample is stored at a temperature below 0° C. but greater than −70° C. (i.e. liquid nitrogen does not need to be used for storage). The storage temperature should be one where the sample remains in a liquid state, which can depend upon the concentration of the cryoprotectant in the sample. In particular embodiments, the sample is stored within a temperature range of about −25° C. to about −5° C. In self-defrosting freezers, temperatures generally travel through this range over a given time period (e.g. about 12 hours).

The cryoprotectant may be any compound that decreases the freezing point of water, thereby preventing ice formation or damage. The composition may contain glycerol or polyethylene glycol as a cryoprotectant. The composition may contain the cryoprotectant in an amount of about 15% by weight to about 65% by weight, or from about 50 wt % to about 65 wt %.

In some particular embodiments, the composition containing the suspended specimen is placed in a container, and a layer of oil is then overlaid on the composition. This can aid in stabilizing the sample, by blocking air from dissolving into the underlying composition.

These and other non-limiting characteristics of the disclosure are more particularly disclosed below.

DETAILED DESCRIPTION

Figure 1:
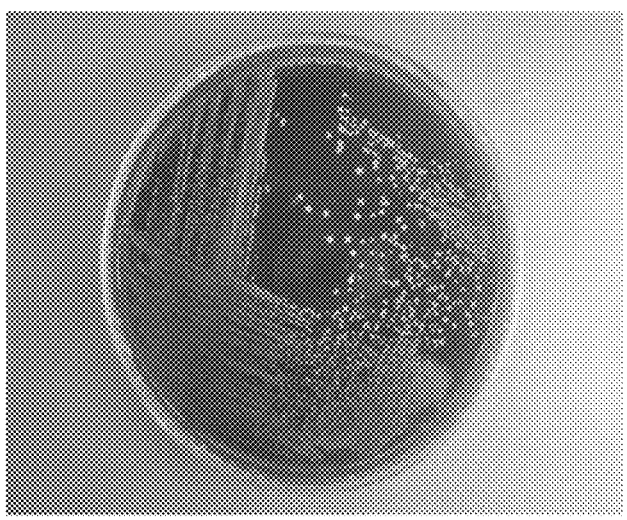
FIG. 1 is a set of images showing an example of a plate plated with the quadrant streak method as well as the plating scheme.
Figure 1:
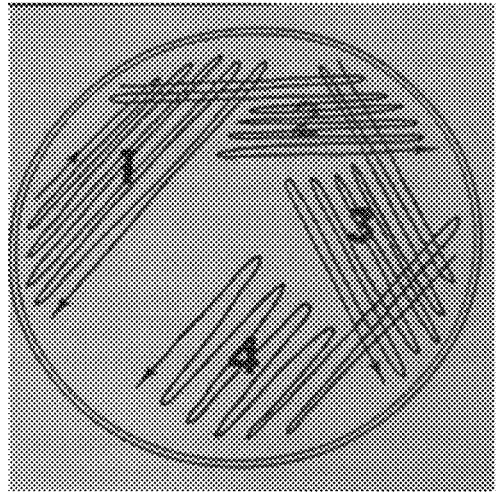

The present disclosure may be understood more readily by reference to the following detailed description of desired embodiments and the examples included therein. In the following specification and the claims which follow, reference will be made to a number of terms which will be defined to have the following meanings.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

"Oxyrase®" is a commercially available enzyme system (from Oxyrase, Inc.) obtained from the cytoplasmic membranes of *Escherichia coli* to produce anaerobic conditions in a wide variety of environments. The system is available in the form of membrane fragments that scavenge oxygen.

The term "cryoprotectant" is used herein to refer to a substance used to protect biological tissue from freezing damage. Examples of cryoprotectants include ethylene glycol, propylene glycol, glycerol, and polyethylene glycol, and dimethyl sulfoxide (DMSO).

The term "polyethylene glycol" is used herein to refer to compounds of the formula $H-(OCH_2CH_2)_n-OH$, where n can be any number from 1 to about 35,000. It is noted though that typical values range from 1 to about 800. It is also noted that in commercially available formulations, the glycols are distributed in a statistical fashion similar to polymers, and the weight-average value of n.

The term "unit" is used herein to refer to a given amount of membrane fragments. One unit is defined as the amount of oxygen scavenging membrane fragments that will reduce dissolved oxygen in one milliliter of air saturated 40 mM phosphate buffer, pH 8.4, at 37 degrees Celsius, at the rate of 1% per second.

For purposes of this disclosure, the terms "anaerobic" and "anaerobe" are used herein to refer specifically to bacteria that will die in the presence of oxygen, i.e. obligate anaerobes, and do not refer to facultative anerobes.

The present application relates to methods for preserving or storing biological specimens, such as anaerobe microorganisms, using compositions comprising oxygen scavenging membrane fragments and cryoprotectants. Said biological specimens may include but are not limited to: stem cells from cord blood and tissue; embryos and larvae for animal husbandry (both farm and aquaculture) and animal reproduction; plant seeds, tissue, and moss; animal cells and tissues; viruses; sperm; stem cells; microorganisms, such as bacteria, fungi, and protozoa; embryos; human oocytes; skin allografts, such as those used in the treatment of severe burn injuries; and tumors. These specimens can be preserved in a vegetative state for long time periods.

The compositions can also include, if desired, a hydrogen donating substance.

The present disclosure removes oxygen through the use of oxygen scavenging membrane fragments. The membrane fragments, which contain an electron transport system that reduces oxygen to water, may be obtained from various sources. It is known that a great number of bacteria have cytoplasmic membranes which contain the electron transport system that effectively reduces oxygen to water if a suitable hydrogen donor is present in the medium. Some suitable bacterial sources include *Escherichia coli, Salmonella typhimurium, Gluconobacter oxydans, Pseudomonas aeruginosa*, and *Acetobacter*. These bacterial membranes have been highly effective in removing oxygen from media and other aqueous and semi-solid environments.

The same oxygen reducing effects produced by the cell membrane fragments from the bacterial sources indicated above can also be obtained by the use of oxygen reducing membranes from, for example, the mitochondrial organelles of a large number of higher non-bacterial organisms. More particularly, a great number of fungi, yeasts, plants, and animals have mitochondria that reduce oxygen to water if a suitable hydrogen donor is present in the medium. Some of the sources of oxygen reducing membranes from these mitochondria are: beef heart muscle, potato tuber, spinach, *Saccharomyces, Neurospora, Aspergillus, Euglena*, and *Chlamydomonas*.

Of all microbes, anaerobes are among the most difficult to isolate, grow, and preserve. Therefore, any damage due to freezing only exacerbates the issue of recovering representative cells from the stored population.

Oxygen scavenging fragments are commercially available as Oxyrase®. Oxyrase® consists of an enzyme system derived from the cytoplasmic membranes of microorganisms. Sterile (EC) and nonsterile (EC/NS) Oxyrase® in particular are derived from the cell membrane fragments of *E. coli* (0.2 microns or smaller) suspended in 20 mM phosphate buffer at a neutral pH. Substrates for Oxyrase® include lactic acid, succinic acid, formic acid, or their salts, and alpha-glycerol phosphate in addition to oxygen. One unit/ml Oxyrase® activity will reduce dissolved oxygen (air saturated 40 mM phosphate buffer, pH 8.4, at 37 degrees Celsius) at the rate of 1% per second. The rate of oxygen removal increases with temperature, and above 55 degrees Celsius, Oxyrase® begins to be inactivated but will persist up to 80 degrees Celsius. Oxyrase® is active over a wide pH range of 6.8 to 8.4.

The exact amount of membranes containing the enzyme systems can vary by a number of parameters. In some embodiments, the composition contains the oxygen scavenging membrane fragments in the amount of about 0.01 units/mL to about 100 units/mL, or from about 0.01 units/mL to about 10 units/mL, or from about 0.3 unit/mL to about 10 units/mL, or from about 1 unit/mL to about 10 units/mL, or from 10 units/mL to 50 units/m L.

Oxyrase® is known to protect cells and aids in the recovery of injured cells. By starving both aerobic and anaerobic cells of oxygen, Oxyrase® places cells in a metabolic resting state, thereby precluding cell growth and replication. The removal of oxygen also aids in the survival of anaerobes. In the case of aerobic cells, the removal of oxygen reduces metabolic activity.

A hydrogen donating substance (i.e., an organic substrate) may be necessary in order for the membrane fragments to perform their oxygen removing functions. Suitable hydrogen donors are lactic acid, succinic acid, alpha-glycerol phosphate, formic acid, malic acid, and where available, their corresponding salts. The hydrogen donating substance may be present in the composition in the amount of about 1 wt % to about 5 wt %.

Cryoprotectants are substances used to protect biological tissue from freezing damage. Typical cryoprotectants include glycerol, dimethyl sulfoxide (DMSO), and glycols, including ethylene glycol, propylene glycol, polyethylene glycol, and glycerol.

In some embodiments, the composition comprises glycerol. Glycerol is a small molecule that can pass through the semipermeable membrane of cells and gain entry into their interior. The cryoprotectant nature of glycerol is available both inside and outside the cell. Glycerol forms strong hydrogen bonds with water molecules, thereby disrupting the crystal lattice formation of ice.

In some embodiments, the composition comprises polyethylene glycol. Polyethylene glycol is another cryoprotectant, impermeable to cell membranes, and can be made at different molecular weights. Its mode of action is limited to the space "outside" a cell. While porins (i.e. channels within a cell membrane) allow movement of small hydrophilic molecules between the interior of a cell and the exterior of a cell, large hydrophilic molecules, such as polyethylene glycol, are too large to pass through the porins. In particular embodiments, the polyethylene glycol has about 400 glycol moieties (designated as PEG 400).

Higher concentrations of cryoprotectants ("high" meaning greater than 15 wt %) can be used to preserve anaerobes. Namely, higher concentrations of cryoprotectants prevent the formation of ice crystals, thereby precluding the freezing of cells and the damage and/or killing of preserved cells. This results in higher numbers of cells being recovered, so that the recovered cells are representative of the initial population that was originally processed. It has been found that microbial cells processed this way and stored at below zero degrees Celsius are still viable after fifteen (15) months of storage.

The composition may contain one or more cryoprotectants in the amount of about 15% to about 65% by weight, or from about 50 wt % to about 65 wt %. This lowers the freezing point of the composition. For example, if 53 wt % of glycerol is used, the freezing temperature of the composition is decreased to −26° C.

The composition also contains water as a solvent for the various ingredients. Desirably, the composition is isotonic. In embodiments, the composition has an osmolality of about 280 milliOsmoles/liter (mOsm/L) to about 300 mOsm/L.

The composition can be used together with a self-defrosting freezer. In such freezers, the temperature cycles up and down within a temperature range. For example, the temperature is brought up from −25° C. to −17° C. for about an hour, then reduced to the lower temperature. This cycle can occur at about 24-hour intervals. Such freezers are significantly cheaper compared to cryogenic freezers. It is noted that the composition remains in a liquid state at these sub-zero temperatures, so that there is reduced damage to the biological specimens that are suspended in the composition.

The present disclosure is further illustrated in the following non-limiting working examples, it being understood that these examples are intended to be illustrative only and that the disclosure is not intended to be limited to the materials, conditions, process parameters and the like recited herein.

EXAMPLES

The following examples both employ the quadrant streak method to determine the efficacy of Oxyrase® in suspensions for preserving and storing biological material. The method consists of streaking the most concentrated inoculum (1 loop-full) onto a restricted area on the surface of a plate (about one-fourth the surface area). The plate is then rotated about 90 degrees in a counter-clockwise direction, and a second quadrant is cross-streaked to overlap the first quadrant. This is done in turn for a third and fourth quadrant as shown in FIG. 1. After incubation, the densest quadrant is the first quadrant and subsequent quadrants have fewer colonies. The furthest quadrant that has well isolated colonies determines the score of the plate. For example, FIG. 1 contains an image of a plate with a score of 4, as the fourth quadrant was the furthest quadrant on the plate with well isolated colonies. Further resolution is designated by adding a + or − to the score (e.g., 4+ or 4−). A + represents a heavily colonized quadrant and a − represents a thinly colonized quadrant. This technique provides a semi-quantitative method to determine viable cell density in the sample and is reliable when comparisons are made for the same individual.

First Set of Experiments

Materials and Methods

Glycerol was used as the cryoprotectant. 266 mL 20 mM phosphate buffer (pH 7.5), 52 mL DL lactic acid (60% syrup (w/w)), 100 grams succinic acid (disodium salt hexahydrate), 0.41 grams cysteine, 66 grams trehalose, and 518 mL glycerol were combined and dissolved. The pH was adjusted with 50% weight by weight sodium hydroxide to a pH of 7.6+/−0.1 at 15 to 20 degrees Celsius. The solution was then sterilized by autoclaving at 121 degrees Celsius for 15 to 20 minutes. After the sterile mixture cooled, Oxyrase® was added to a final activity of 30 u/mL and gently mixed. The mixture was then aseptically distributed in volumes of 5.0 mL into sterile, screw-cap scintillation vials. Five vials were tested for sterility at 37 degrees Celsius for seven days. Vials containing the liquid mixture were then stored at −20 degrees Celsius.

To preserve anaerobic microorganisms, the frozen single vial was pre-warmed to room temperature. A heavy suspension of cells was created from a PRAS Brucella plate or a Schaedler OxyPlate from the confluent quadrant of a quadrant streaked plate in 1 mL of sterile 20 mM phosphate buffer (pH 7.6). The cell suspension was then aseptically transferred to the pre-warmed vial and gently mixed to disperse. The vial was then incubated at 37 degrees Celsius for 30 minutes before placing the vial containing the suspension into a freezer at −20 degrees Celsius. Incubation allows Oxyrase® to reduce any oxygen that is present and makes for a reduced storage environment. After seven days, one loop of mixed suspension was aseptically taken from the vial and an appropriate plate was quadrant streaked. The plate was then incubated at 37 degrees Celsius and observed at 24 hours, 48 hours, and 72 hours.

Suspensions containing Oxyrase® and microbes were prepared. Particularly, suspensions were prepared for *B. fragilis, C. perfringens, F. nucleatum, P. levii, P. anaerobius, B. adolescentis, P. melaninogenica, S. aureus, P. mirabilis,* and *E. coli.* At specified monthly intervals over the course of a year, a loopful of suspension was aseptically removed from the storage vial and was quadrant streaked on a PRAS Brucella plate. Plates containing anaerobes were incubated at 37 degrees Celsius in an anaerobic jar with a catalyst to remove oxygen and observed at an appropriate time.

Some months later, two additional Oxyrase® suspensions were created. One suspension contained *F. nucleatum* with oil while the other suspension contained *P. melaninogenica* with oil.

Figure 2:
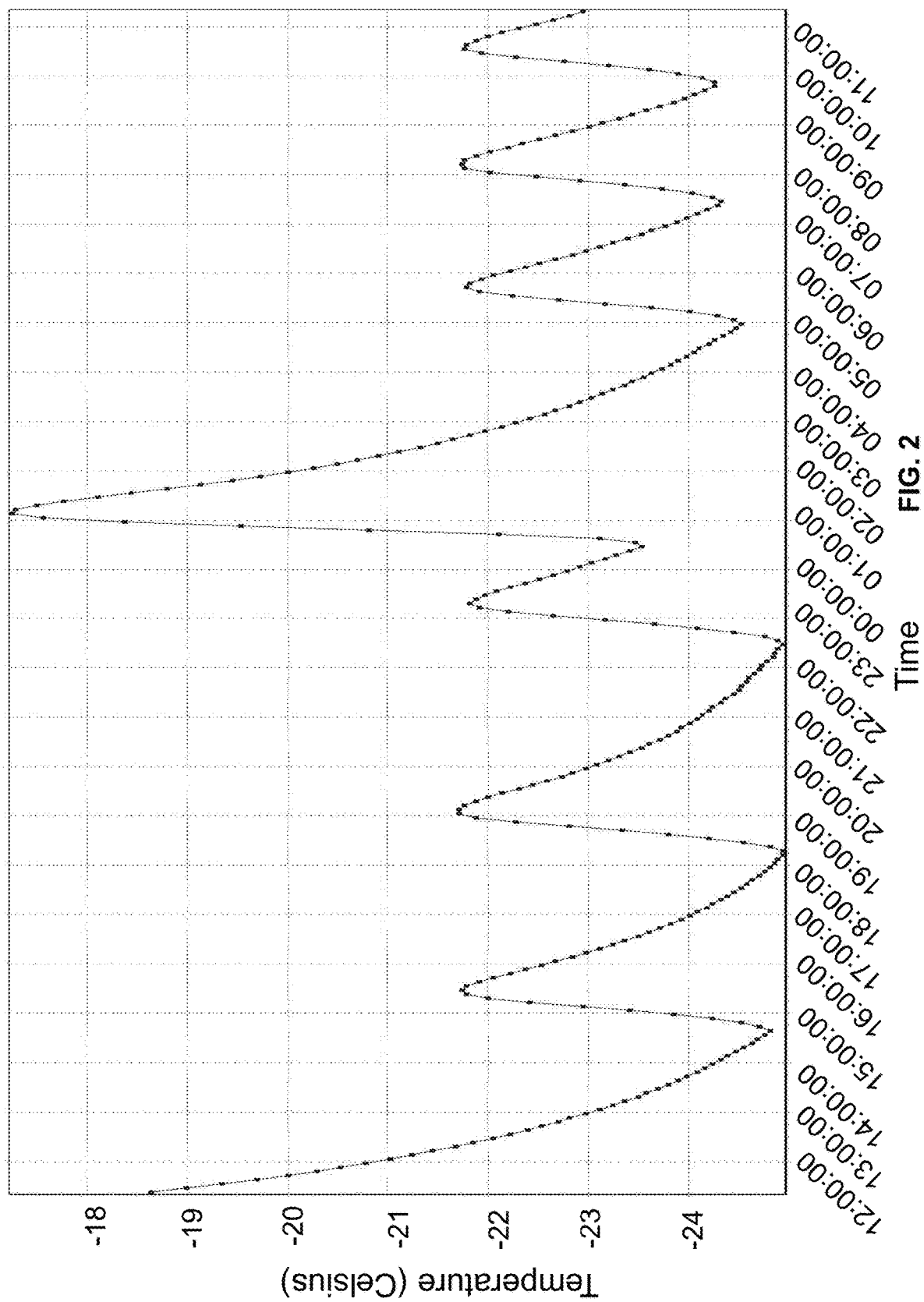
FIG. 2 is a graph indicating the temperature cycle of the self-defrosting freezer holding the stored suspensions containing Oxyrase® and the test microbes.

The microbes stored in the Oxyrase® suspension were stored in a self-defrosting freezer, which meant the temperature was brought to −17 degrees Celsius and then returned to −20 degrees Celsius or below. The freezer cycled about every 24 hours. As shown in FIG. 2, the temperatures ranged over a high of −17 degrees Celsius to a low of −25 degrees Celsius. In addition, there were smaller cycles from −25 degrees Celsius to −22 degrees Celsius over a 3-hour period. It is noted that the temperature ranges for the freezer refer to the ambient temperature inside the freezer. The walls of the freezer may be at a different temperature (e.g. to affect defrosting), and the temperature of items inside the freezer may also be different.

Results

Tables 1-3 below express the results of the monthly quadrant streak tests for the microbes in suspension with Oxyrase® and glycerol. They are reported by the month of sampling. In some assays, the colony counts were limited to the first quadrant and had few colonies (less than a 1−). These were counted and listed as colony-forming units (cfu).

TABLE 1

Recovery of Microbes Stored in Glycerol Base with Oxyrase ® at −20 Degrees Celsius for 5 Months. Set A

| Initial Score | Microbe | 1 month | 2 months | 3 months | 4 months | 5 months |
|---|---|---|---|---|---|---|
| 4+ | *B. fragilis* | 4 | 4 | 4 | 4+ | 4 |
| 3+ | *C. perfringens* | 3− | 2+ | 2+ | 3+ | 2+ |

TABLE 1-continued

Recovery of Microbes Stored in Glycerol Base with Oxyrase ® at −20 Degrees Celsius for 5 Months. Set A

| Initial Score | Microbe | 1 month | 2 months | 3 months | 4 months | 5 months |
|---|---|---|---|---|---|---|
| 3+ | *F. nucleatum* | 3− | 2 | 2+ | 1+ | 3− |
|  | *F. nucleatum* with oil |  |  |  | 4 | 2+ |
| 3+ | *P. levii* | 4 | 4− | 3+ | 3+ | 3+ |
| 4+ | *P. anaerobius* | 3+ | 3+ | 3+ | 4 | 3 |
| 4 | *B. adolescentis* | 3+ | 4− | 3− | 3− | 3 |
| 3 | *P. melaninogenica* | 3+ | 2+ | 2+ | 1+ | 2+ |
|  | *P. melaninogenica* with oil |  |  |  | 4 | 2+ |
| 4− | *S. aureus* | 4− | 4+ | 4+ | 4 | 4 |
| 4 | *P. mirabilis* | 4− | 4− | 4+ | 4− | 4+ |
| 4 | *E. coli* | 4 | 4− | 4− | 4 | 4 |

TABLE 2

Recovery of Microbes Stored in Glycerol Base with Oxyrase ® at −20 Degrees Celsius for 10 Months Set B

| Initial Score | Microbe | 6 month | 7 month | 8 month | 9 month | 10 month |
|---|---|---|---|---|---|---|
| 4+ | *B. fragilis* | 4+ | 4 | 4− | 3+ | 3+ |
| 3+ | *C. perfringens* | 3− | 3− | 3− | 3 | 3 |
| 3+ | *F. nucleatum* | NG/2 cfu | 2 cfu/2 | NG | NG/1+ | NG/2− |
|  | *F. nucleatum* with oil | 2 | 2 | 1+ | 1+ | 2− |
| 3+ | *P. levii* | 3+ | 4 | 3+ | 3 | 3− |
| 4+ | *P. anaerobius* | 3+ | 4 | 3+ | 3+ | 2+ |
| 4 | *B. adolescentis* | 3+ | 3 | 3− | 3− | 3+ |
| 3 | *P. melaninogenica* | NG/2+ | 6 cfu/2+ | 1+ | NG/2+ | 1+ |
|  | *P. melaninogenica* with oil | 2+ | 3+ | 1+ | 1 | 2− |
| 4− | *S. aureus* | 4+ | 4+ | 4+ | 4+ | 4 |
| 4 | *P. mirabilis* | 4+ | 4+ | 4 | 3+ | 4 |
| 4 | *E. coli* | 3+ | 3+ | 4− | 3+ | 4 |

TABLE 3

Recovery of Microbes Stored in Glycerol Base with Oxyrase ® at −20 Degrees Celsius for 15 Months Set C

| Initial Score | Microbe | 11 month | 12 month | 15 month |
|---|---|---|---|---|
| 4+ | *B. fragilis* | 3+ | 4 | 3+ |
| 3+ | *C. perfringens* | 3+ | 3− | 3 |
| 3+ | *F. nucleatum* | 1+ | 2cfu/2 | NG/1+ |
|  | *F. nucleatum* with oil | 2− | 2− | 2− |
| 3+ | *P. levii* | 2+ | 4 | 3 |
| 4+ | *P. anaerobius* | 2+ | 4 | 3+ |
| 4 | *B. adolescentis* | 1+ | 3 | 3− |
| 3 | *P. melaninogenica* | NG/2+ | 6cfu/2+ | NG/2+ |
|  | *P. melaninogenica* with oil | 2− | 2− | 2− |
| 4− | *S. aureus* | 4 | 4+ | 4+ |
| 4 | *P. mirabilis* | 4 | 4+ | 3+ |
| 4 | *E. coli* | 4 | 3+ | 3+ |

With respect to Tables 1-3, NG/2+ denotes that after a first determination, there was no growth, but after a second determination, growth was scored at 2+. In such a case, the second determination was made as the first determination led to a suspect first result. Also with respect to Tables 1-3, 2 cfu/2 denotes that after a first determination, two colony forming units (cfu) were observed, and after a second determination, growth was scored at 2.

As shown, suspensions containing Oxyrase® exhibited consistent recovery scores over the course of at least fifteen months. The only exceptions were *F. nucleatum, P. levii*, and *P. melaninogenica*, which are difficult microbes to suspend uniformly. Several values are noted as "NG," which are indicative of "no growth." Often the measured value returned upon sampling the next month. This is due to aggregation of these microbes and uneven sampling, not due to changes in viability.

The recovered cells remained undamaged as the cells and medium did not freeze during preparation and storage.

Second Sets of Experiments

Materials and Methods

Polyethylene glycol was used as the cryoprotectant. 266 mL 20 mM phosphate buffer (pH 7.5), 52 mL DL lactic acid (60% syrup (w/w)), 100 grams succinic acid (disodium salt hexahydrate), 0.41 grams cysteine, 66 grams trehalose, and 518 mL polyethylene glycol (PEG 400) were combined and dissolved. The pH was adjusted with 50% weight by weight sodium hydroxide to a pH of 7.6+/−0.1 at 15 to 20 degrees Celsius. The solution was then sterilized by autoclaving at 121 degrees Celsius for 15 to 20 minutes. After the sterile mixture cooled, Oxyrase® was added to a final activity of 30 u/mL and gently mixed. The mixture was then aseptically distributed in volumes of 5.0 mL into sterile, screw-cap scintillation vials. Five vials were tested for sterility at 37 degrees Celsius for seven days. Vials containing the liquid mixture were then stored at −20 degrees Celsius.

To preserve microorganisms, the frozen single vial was pre-warmed to room temperature. A heavy suspension of cells was created from a PRAS Brucella plate or a Schaedler OxyPlate from the confluent quadrant of a quadrant streaked plate in 1 mL of sterile 20 mM phosphate buffer (pH 7.6). The cell suspension was then aseptically transferred to the pre-warmed vial and gently mixed to disperse. The vial was then incubated at 37 degrees Celsius for 30 minutes before placing the vial containing the suspension into a freezer at −20 degrees Celsius. Incubation allows Oxyrase® to reduce any oxygen that is present and makes for a reduced storage environment. After seven days, one loop of mixed suspension was aseptically taken from the vial and an appropriate plate was quadrant streaked. The plate was then incubated at 37 degrees Celsius and observed at 24 hours, 48 hours, and 72 hours.

Suspensions containing Oxyrase® and microbes were prepared. Particularly, suspensions were prepared for *B. fragilis, C. perfringens, F. nucleatum, P. levii, P. anaerobius, B. adolescentis, P. melaninogenica, S. aureus, P. mirabilis*, and *E. coli*. At specified monthly intervals over the course of eight months, a loopful of suspension was aseptically removed from the storage vial and was quadrant streaked on a PRAS Brucella plate. Plates containing anaerobes were incubated at 37 degrees Celsius in an anaerobic jar with a catalyst to remove oxygen and observed at an appropriate time.

The microbes stored in the Oxyrase® suspension were stored in a self-defrosting freezer, which cycled about every six hours. As shown in FIG. 2, the temperatures ranged over a high of −17 degrees Celsius to a low of −25 degrees Celsius.

Results

Table 4 below expresses the results of the monthly quadrant streak tests for the microbes in suspension with Oxyrase® and Polyethylene Glycol.

TABLE 4

Recovery of Microbes Stored in PEG Base with Oxyrase ® up to 8 Months at −20 Degrees Celsius.

| Initial Score | Microbe | Time Stored (Months) | | | | | | | |
|---|---|---|---|---|---|---|---|---|---|
| | | 1 | 2 | 3 | 4 | 5 | 6 | 7 | 8 |
| 4 | B. fragilis | 4 | 4− | 4+ | 4 | 4 | 4 | — | 2 |
| 2+ | C. perfringens | 3− | 3+ | 4 | 3 | 3+ | 3 | — | 3 |
| 2 | F. nucleatum | 1+ | 2+ | 2 | 2 | 2 | 2 | — | NG |
| 2 | P. levii | 4+ | 4+ | 4 | 4 | 4 | 3+ | — | 3 |
| 3− | P. anaerobius | 4− | 4− | 4 | 4− | 4− | 4 | — | 2+ |
| 3 | B. adolescentis | 3+ | 4 | 4 | 4 | 4 | 4 | — | 4− |
| 1+ | P. melaninogenica | 2 | 2+ | 3 | 2 | 2 | 2− | — | NG |
| 4 | S. aureus | 4 | 4 | 4+ | 4 | 4 | 4 | — | 4 |
| 3+ | P. mirabilis | 4 | 4 | 4 | 4 | 4 | 4 | — | 4+ |
| 3+ | E. coli | 3+ | 4 | 4 | 3+ | 3+ | 3+ | — | 3+ |

Like the results of the first experiment, the results of the second experiment indicate suspensions containing Oxyrase® lead to higher and more consistent recovery rates of stored biological specimens. The ratios of recovered cells to initial cells were very high, often greater than 75% of the initial value.

Sampling issues are again apparent throughout the table, particularly with respect to the challenging anaerobes *F. nucleatum* and *P. melaninogenica*. There is no indication that viability dropped as time of storage increased.

Discussion

As shown in Tables 1-4 above, microbial suspensions containing a particular concentration of cryoprotectant and Oxyrase® succeeded in preserving and storing biological specimens under sub-zero conditions for a prolonged period of time. The consistent recovery of specimens after holding them at freezing temperatures has been achieved by using high concentrations of cryoprotectants to lower the freezing point of the mixture used to preserve the cells. For example, if glycerol were used in a medium at 53% by weight, then the freezing temperature decreases to −26 degrees Celsius. A standard freezer operates at −20 degrees Celsius.

Here a panel of microorganisms in a medium containing 53% glycerol has been stored for a period of 15 months in a standard freezer. The medium did not freeze, and high numbers of viable cells were consistently recovered from the preserved cells. The microbial cells were not adversely affected by the high concentration of glycerol.

Some of the anaerobic microbes tested are the most difficult of microbes to isolate, grow and preserve, particularly *F. nucleatum, P. levii*, and *P. melaninogenica*. It should be noted that the recovery scores remained consistent through the storage period with the exception of these challenging microbes. Sampling these microbes is problematic, as they are difficult to suspend uniformly. Every effort was made to keep the sampling time as short as possible so as to not lose viability due to exposure to ambient air. These sampling problems can particularly be seen across the *F. nucleatum* samples. Note some of the values drop to zero, or no growth, as indicated by "NG" and then a positive value is obtained on the next sample. This reflects the difficulty in obtaining uniform samples rather than a loss in viability.

Some of this variability can be overcome by using a different or improved technique. For example, if sterile oil is overlaid onto the suspension liquid containing Oxyrase® and a microbe in the vial, subsequent samples become more stable and consistent in numbers recovered. This is shown in the rows of Tables 1 and 2 corresponding to *F. nucleatum* with oil and *P. melaninogenica* with oil. The greater stability and consistency is due to the oil blocking air (and subsequently oxygen) from dissolving into the underlying suspension, thereby protecting the stored microbe from the deleterious effect of oxygen.

Unlike other storage methods, such as lyophilization, the majority of microbes that went into storage using the Oxyrase® suspension were recovered (>>1:100). Other storage methods have exhibited recovery of anaerobes at the level of one in a million or less. Under conditions disclosed in this application, using cryoprotectant and Oxyrase® suspension conditions, the recovered microorganism is highly likely to be representative of the population put into storage. In contrast, lyophilization and cryopreservation suffer from reduced recovery, and any cells recovered are not likely to be representative of the population initially stored.

The superior recovery of cells stored in the Oxyrase® suspension is due to the cells not freezing. The cryoprotectant, in the first case glycerol, is neither toxic nor harmful to the microbes. Not only are the microbes spared the detrimental effects of freezing and thawing, but they are also always kept at sub-freezing temperatures, which contributes to the stability of the stored samples.

As mentioned above, FIG. 2 shows the temperature ranges through which the storage freezer cycled. However, despite the fluctuation in temperature, the data in Tables 1 and 2 show that the viability of the stored microbes is relatively constant, even taking into account sampling issues. During storage, cells were always at sub-freezing temperatures, and at these temperatures, the cells were in a static state, which contributed to the storage stability of the cells.

As stated above, PEG400 is impermeable to the cell membrane. However, despite its limited action to the outside of a cell, the cell and its contents reside at subzero temperatures in suspension. The results of the second experiment thereby support the interpretation that cell contents do not freeze at these temperatures. Damage due to freezing and thawing, when it occurs, must take place outside the membrane.

The contents inside a cell are very different from the solutes and solutions encountered in a laboratory. For example, the DNA chromosome of a representative microbe such as *E. coli* is millions of base pairs long and is greater than $10^9$ daltons in mass. Often a cell contains two such molecules. These molecules, in addition to transfer RNAs, ribosomes, and proteins, are contained in a compartment 3-5 μm in length and 2-3 μm in diameter. It would not be surprising to find that the contents of microbial cells do not freeze at typical freezer temperatures.

Storing suspensions in a liquid state makes working with them easier and simpler, as samples can quickly and simply be removed from a vial. For more difficult anaerobes, the liquid suspensions make possible maintenance and storage, which translates into higher inefficiencies and lower costs.

Being able to maintain stored cells in a self-defrosting freezer contributes to the reduced effort needed to maintain a collection. Costs are kept to a minimum when multiple freezers are used, and savings result from the lower labor cost in maintaining freezers and not having to defrost them. In addition to reduced labor costs that result from storage of biological collections with suspensions containing Oxyrase®, the costs for the equipment are substantially reduced, as standard household freezers are thousands of dollars cheaper than the costs of cryofreezers. Therefore, the application significantly reduces the cost and labor associated with preserving biological materials.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A method for storing biological specimens, comprising (i) suspending a sample of the biological specimens in a composition comprising a cryoprotectant and oxygen scavenging membrane fragments; and (ii) storing the sample suspended in the composition at a temperature below 0° C., wherein the composition remains in a continuous liquid state throughout storage;
   wherein the cryoprotectant is ethylene glycol, propylene glycol, glycerol, a polyethylene glycol, or dimethyl sulfoxide (DMSO); and
   wherein the composition contains from about 15 wt % to about 65 wt % of the cryoprotectant.

2. The method of claim 1, wherein the oxygen scavenging membrane fragments are derived from the cytoplasmic membranes of *Escherichia coli, Salmonella typhimurium, Gluconobacter oxydans, Pseudomonas aeruginosa,* or *Acetobacter*.

3. The method of claim 1, wherein the composition further comprises a hydrogen donating substance.

4. The method of claim 3, wherein the hydrogen donating substance is lactic acid, succinic acid, alpha-glycerol phosphate, formic acid, malic acid, or a salt thereof.

5. The method of claim 3, wherein the hydrogen donating substance is present in the amount of about 1 wt % to about 5 wt % of the composition.

6. The method of claim 1, wherein the composition is in the form of a suspension.

7. The method of claim 1, wherein the composition contains the oxygen scavenging membrane fragments in an amount greater than 0.01 units per milliliter or greater than 0.5 units per milliliter, or greater than 1 unit per milliliter, or from 1 unit per milliliter to 10 units per milliliter, or from 5 units per milliliter to 10 units per milliliter, or from 10 units per milliliter to 50 units per milliliter.

8. The method of claim 1, wherein the sample is stored at a temperature range of from about −25° C. to about −5° C.

9. The method of claim 1, wherein the cryoprotectant is glycerol or a polyethylene glycol.

10. The method of claim 1, wherein the composition is first placed in a container, and an oil layer is then overlaid onto the composition.

11. The method of claim 1, wherein the biological specimens are anaerobe bacteria selected from the group consisting of *Bacteroides fragilis, Bifidobacterium adolescentis, Clostridium perfringens, Fusobacterium nucleatum, Porphyromonas levii, Peptostreptococcus anaerobius, Prevotella melaninogenica,* and combinations thereof.

* * * * *